United States Patent [19]

Gaughan et al.

[11] 4,334,911
[45] Jun. 15, 1982

[54] HERBICIDAL COMPOSITIONS AND METHODS

[75] Inventors: Edmund J. Gaughan, Berkeley; Ferenc M. Pallos, Walnut Creek, all of Calif.

[73] Assignee: Stauffer Chemical Company, Westport, Conn.

[21] Appl. No.: 849,140

[22] Filed: Nov. 7, 1977

Related U.S. Application Data

[63] Continuation-in-part of Ser. No. 721,721, Sep. 13, 1976, abandoned, which is a continuation-in-part of Ser. No. 619,114, Oct. 2, 1975, abandoned.

[51] Int. Cl.³ ............................................. A01N 25/32
[52] U.S. Cl. .......................................... 71/93; 71/100; 71/103
[58] Field of Search ........................... 71/93, 100, 103

[56] References Cited

U.S. PATENT DOCUMENTS 3,799,760  3/1974  Stephens ............................. 71/103
3,933,894  1/1976  Stephens ............................. 260/470

FOREIGN PATENT DOCUMENTS 846894  4/1977  Belgium .

Primary Examiner—Catherine L. Mills
Attorney, Agent, or Firm—Harry A. Pacini

[57] ABSTRACT

Soybeans are protected against injury from a herbicidal mixture comprising a thiocarbamate and a triazine by use of certain N-benzenesulfonyl carbamates as herbicide antidotes. The N-benzenesulfonyl carbamates have the general structural formula

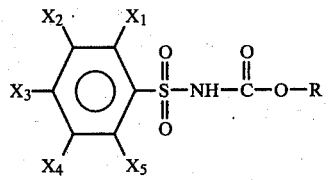

wherein each of $X_1$, $X_2$, $X_3$, $X_4$ and $X_5$ is independently selected from the group consisting of hydrogen, halogen and lower alkyl, with the proviso that when $X_3$ is lower alkyl, $X_1$ and $X_5$ are not both hydrogen; and R is selected from the group consisting of lower alkyl, alkenyl, alkynyl and alkyl and alkenyl radicals substituted with up to five halo atoms.

10 Claims, No Drawings

HERBICIDAL COMPOSITIONS AND METHODS

This is a continuation-in-part of co-pending application Ser. No. 721,721 filed Sept. 13, 1976, abandoned, which in turn is a continuation-in-part of Ser. No. 619,114, filed Oct. 2, 1975 now abandoned.

BACKGROUND OF THE INVENTION

This invention relates to the use of certain N-benzene-sulfonyl carbamates as herbicide antidotes to protect soybeans against injury from a thiocarbamate-triazine herbicidal mixture. Herbicidal mixtures of this type are frequently used to obtain desired control of both grasses and broad-leaf weeds.

DESCRIPTION OF THE PRIOR ART

Certain N-benzenesulfonyl carbamates are disclosed in U.S. Pat. No. 3,799,760, J. A. Stephens, Mar. 26, 1974 and U.S. Pat. No. 3,933,894, J. A. Stephens, Jan. 20, 1976 to be useful as herbicides. Belgian Pat. No. 846,894, Stauffer Chemical Company, Apr. 1, 1977, reports the use of N-benzenesulfonyl carbamates as herbicidal antidotes to protect crops from injury by thiocarbamate type herbicides.

DESCRIPTION OF THE INVENTION

N-benzenesulfonyl carbamates of the general structural formula

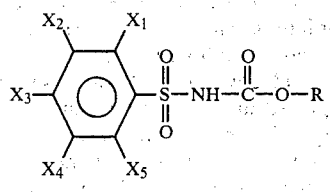

wherein each of $X_1$, $X_2$, $X_3$, $X_4$ and $X_5$ is independently selected from the group consisting of hydrogen, halogen and lower alkyl, with the proviso that when $X_3$ is lower alkyl, $X_1$ and $X_5$ are not both hydrogen; and R is selected from the group consisting of lower alkyl, alkenyl, alkynyl and alkyl and alkenyl radicals substituted with up to five halo atoms are effective antidotes for protecting soybeans from injury by a herbicidal mixture comprising thiocarbamate and triazine herbicides.

In the above definitions, the term lower alkyl refers to straight and branched chain alkyl radicals having 1 to 4 carbon atoms, i.e., methyl, ethyl, propyl, isopropyl, butyl, isobutyl, sec-butyl and tert-butyl. The term alkenyl refers to straight and branched chain alkenyl radicals containing 3 to 6 carbon atoms, for example propen-1-yl, 3-methylpropen-1-yl, buten-1-yl, penten-1-yl, hexen-1-yl, and position isomers thereof. The term alkynyl refers to straight and branched chain alkynyl radicals containing 3 to 6 carbon atoms, for example, propyn-1-yl, 1-methylpropyn-2-yl, 1-methylbutyn-2-yl, butyn-1-yl, pentyn-1-yl, hexyn-1-yl, and positions isomers thereof. The term haloalkyl and the term haloalkenyl refer to alkyl and alkenyl radicals as defined above substituted with up to five, and preferably up to three, halo atoms. Halo includes chlorine, bromine, fluorine and iodine, with chlorine and fluorine being preferred.

Particularly preferred are compounds in which each of $X_1$, $X_2$, $X_4$ and $X_5$ are hydrogen, $X_3$ is hydrogen, chlorine or bromine and R is as defined above. Another preferred subgenus includes compounds in which $X_1$, $X_3$, and $X_5$ are lower alkyl, particularly methyl, and R is as defined above. Still another preferred subgenus includes those compounds in which $X_1$, $X_2$, $X_4$ and $X_5$ are hydrogen, $X_3$ is hydrogen, chlorine or bromine and R is methyl, ethyl, isopropyl, 2,2-dichloroethyl, 2,2,2-trichloroethyl, 2,2,2-trifluoroethyl, allyl, 2-chloroallyl, propargyl or 2-butyn-1-yl.

Illustrative examples of suitable N-benzenesulfonyl carbamates are: N-(4-chlorobenzenesulfonyl)-propargyl carbamate, N-(4-chlorobenzenesulfonyl)-ethyl carbamate, N-(4-chlorobenzenesulfonyl)-2,2-dichloroethyl carbamate, N-(4-chlorobenzenesulfonyl)-2,2,2-trifluoroethyl carbamate, N-(4-chlorobenzenesulfonyl)-2-chloroallyl carbamate, N-(4-chlorobenzenesulfonyl)-2-butyn-1-yl carbamate, N-(benzenesulfonyl)-propargyl carbamate, N-(4-bromobenzenesulfonyl)-propargyl carbamate, N-(4-chlorobenzenesulfonyl)-allyl carbmate, N-(benzenesulfonyl)-2,2,2-trifluoroethyl carbamate, N-(4-chlorobenzenesulfonyl)-methyl carbamate, N-(2,4,6-trimethylbenzenesulfonyl)-propargyl carbamate, N-(benzenesulfonyl)-isopropyl carbamate, N-(3-chlorobenzenesulfonyl)-2,2,2-trifluoroethyl carbamate, N-(benzenesulfonyl)-2,2,2-trichloroethyl carbamate, N-(3,5-dichlorobenzenesulfonyl)-propargyl carbamate, N-(3-methylbenzenesulfonyl)-2,2-dichloroethyl carbamate, N-(2,4,6-triethylbenzenesulfonyl)-allyl carbamate, N-(2-isopropylbenzenesulfonyl)-2-chloroallyl carbamate, N-(4-iodobenzenesulfonyl)-propyl carbamate, N-(4-iodobenzenesulfonyl)-propargyl carbamate, N-(3,5-dimethylbenzenesulfonyl)-2,2,2-trifluoroethyl carbamate, N-(2,6-diethylbenzenesulfonyl)-propargyl carbamate and N-(2,4,6-trichlorobenzenesulfonyl)-2-butyn-1-yl carbamate.

The N-benzenesulfonyl carbamates utilized in accordance with the instant invention can be prepared by known methods. One general method of preparing N-benzenesulfonyl alkynyl carbamates is the reaction of an appropriate alkynol with benzenesulfonyl isocyanate. More particularly, the reaction is performed in the presence of a solvent such as benzene or chloroform with catalytic amounts of triethylamine and dibutyl tin dilaurate. In some instances, a catalyst is not required. After the reaction is complete, the product is recovered by filtration or evaporation of the solvent. If necessary, the product can be recrystallized from a suitable solvent.

A general method for preparing N-benzenesulfonyl alkyl carbamates is the reaction of an appropriate benzenesulfonamide with an alkyl chloroformate in the presence of potassium carbonate. A solvent is normally employed to facilitate the reaction and aid in the work-up of the product. After filtration, extraction and drying, the product can be purified further by trituration with hexane or recrystallization from a suitable solvent.

The following example illustrate the preparation of N-benzenesulfonyl carbamates.

EXAMPLE 1

Preparation of N-(p-chlorobenzenesulfonyl)-propargyl carbamate.

To a solution of 1.7 grams (0.03 mole) of propargyl alcohol in 20 milliliters of benzene containing one drop of triethylamine and one drop of dibutyl tin dilaurate was added a solution of 6.5 grams (0.03 mole) p-chlorobenzenesulfonyl isocyanate in 25 milliliters benzene. The reaction was exothermic and the temperature was allowed to rise to 30° C. The mixture was stirred several hours at room temperature and the precipitated solid was filtered and washed with a small amount of hexane and dried. There was obtained a yield of 8.0 grams (98% of theory) of the title compound, m.p. 106°–108° C. A pure sample melted at 120.5°–121° C. The structure was confirmed by infrared (IR), nuclear magnetic resonance (NMR) and mass spectroscopy (MS).

EXAMPLE 2

Preparation of N-(p-chlorobenzenesulfonyl)-ethyl carbamate p-Chlorobenzenesulfonamide (6.1 grams, 0.032 mole), potassium carbonate (10.8 grams, 0.078 mole), and ethyl chloroformate (3.7 grams, 0.034 mole) in 40 milliliters of acetone were stirred and refluxed for two hours. During the heating period the mixture became thick and was diluted with another 30 milliliters of acetone. The cooled mixture was poured into 150 milliliters of water and filtered through Celite. The filtrate was acidified with hydrochloric acid with cooling (pH about 2) and the product extracted with benzene. The extract was washed with water and dried over anhydrous magnesium sulfate. Removal of the solvent left the title compound as a solid. There was obtained a yield of 5.5 grams (65% of theory) of the title compound, m.p. 85°–90° C. The structure was confirmed by IR.

The use of these compounds as antidotes to protect soybeans (*Glycine max*) from injury by a herbicidal mixture comprising S-n-propyl-di-n-propyl thiocarbamate (VERNAM®) and 2-chloro-4-ethylamino-6-isopropylamino-s-triazine (atrazine) is demonstrated by the following evaluation procedure.

EXAMPLE 3

The following stock solutions of herbicide and each antidote were:

ANTIDOTE STOCK SOLUTION

Sixty-eight milligrams of each antidote compound to be tested was dissolved in 50 milliliters (ml) of acetone to provide a solution such that 1.0 ml is equivalent to a rate of 0.5 pounds per acre (lb/A); 2.0 ml would be equivalent to 1.0 lb/A, and 4.0 ml would be equivalent to 2.0 lb/A when applied to a 5"×7" flat.

HERBICIDE STOCK SOLUTIONS

S-n-propyl-di-n-propyl thiocarbamate (VERNAM®)

Four hundred twenty-two milligrams of VERNAM 6E was dissolved in 125 ml of water to provide a solution such that 5.0 ml would be equivalent to 5.0 lb/A and 304 milligrams VERNAM 6E were dissolved in 75 ml water to provide a solution such that 5.0 ml would be equivalent to 6.0 lb/A when applied to a 5"×7" flat.

2-chloro-4-ethylamino-6-isopropylamino-s-triazine (AATREX®)

Fifty-one milligrams of AAtrex 80W was dissolved in 150 ml of water to provide a solution such that 1 ml would be equivalent to a rate of 0.1 lb/A, 2.5 ml would be equivalent to a rate of 0.25 lb/A and 5.0 ml would be equivalent to a rate of 0.5 lb/A when applied to a 5"×7" flat.

PREPLANT INCORPORATION (TANK MIX) EVALUATION

Small flats were filled with Felton loamy sand soil. The soil from each flat was transferred to a five gallon cement mixer. A tank mix was prepared by mixing the appropriate quantities of herbicide and antidote stock solutions to provide the application rates specified in Table I. The tank mix was then added to the soil while in the cement mixer to simultaneously incorporate both herbicide and antidote into the soil. The soil was transferred back into the flats. Control flats of soil containing only herbicide were similarly prepared for use in comparison ratings.

One pint of soil was removed from each flat and reserved for later use in covering the seeds. Rows ¼ inch deep were made lengthwise in the flats, soybean seeds were added and covered with the reserved soil. The flats were placed in a greenhouse and maintained at a temperature of 70°–90° F. Flats were watered by sprinkling as needed. Injury ratings of the antidote treated and control flats were taken after four weeks. The results are reported in Table I as percent injury of soybeans in the antidote treated flat/ the percent injury of soybeans in the control flat.

In addition to soybeans, mustard (*Brassica juncea*) and watergrass (*Eichinchloa crusgalli*) seeds were planted in the treated and control flats. Some protection of mustard by the antidote test compound in the treated flats was noted at a rate of 6 lb/A VERNAM and 0.1 lb/A AAtrex. No protection of watergrass at any of the applied rates of the herbicide and antidotes was observed.

TABLE I

| Antidote Compound | VERNAM Rate (lb/A) | AATREX Rate (lb/A) | Results at Indicated Antidote Rates | | |
|---|---|---|---|---|---|
| | | | 0.5 lb/A | 1.0 lb/A | 2.0 lb/A |
| N-(p-chlorobenzene-sulfonyl)-propargyl carbamate | 5 | .1 | 50/85 | 30/85 | 0/85 |
| | 5 | .25 | 100/100 | 100/100 | 60/100 |
| | 5 | .5 | 100/100 | 100/100 | 100/100 |
| | 6 | .1 | | | 40/75 |
| | 6 | .25 | | | 60/90 |
| | 6 | .5 | | | 100/100 |
| N-(p-chlorobenzene-sulfonyl)-ethyl carbamate | 5 | .1 | 10/85 | 0/85 | 0/85 |
| | 5 | .25 | 60/100 | 0/100 | 0/100 |
| | 5 | .5 | 100/100 | 70/100 | 40/100 |
| | 6 | .1 | | 80/100 | 80/100 |
| | 6 | .25 | | 100/100 | 70/100 |
| | 6 | .5 | | 100/100 | 100/100 |
| | 6 | .1 | | | 0/75 |
| | 6 | .25 | | | 10/90 |
| | 6 | .5 | | | 100/100 |

The above example illustrates the use of certain N-benzenesulfonyl carbamates as herbicide antidotes to protect soybeans from injury by a herbicidal mixture comprising S-n-propyl di-n-propyl thiocarbamate and 2-chloro-4-ethylamino-6-isopropylamino-s-triazine by applying the antidote and herbicides as a tank mix. The use of other thiocarbamate and triazine herbicides and other methods of application can be used, if desired. Numerous thiocarbamate herbicides are well known, for example, S-ethyl N,N-di-n-propyl thiocarbamate, S-n-propyl N,N-di-n-propyl thiocarbamate, S-ethyl N,N-diisobutyl thiocarbamate, S-ethyl N-cyclohexyl-N-ethyl thiocarbamate, S-n-propyl N-n-butyl-N-ethyl thiocarbamate, S-ethyl hexahydro-1H-azepine carbothioate, S-isopropyl hexahydro-1H-azepine carbothioate, 2,3,3-trichloroallyl N,N-diisopropyl thiocarbamate and S-isopropyl-1-(5-phenyl-2-methylpiperidine) carbothioate. Other triazine herbicides include, for example, 2-(4-chloro-6-ethylamino-s-triazin-2-yl-amino)-2-methylpropionitrile, 2,4-bis(isopropylamino)-6-methylthio-s-triazine, 2-[(4-chloro-6-cyclopropylamino-1,3,5-triazin-2-yl)-amino]-2-methylpropionitrile, 2-ethylamino-4-isopropylamino-6-methylthio-s-triazine, 2-chloro-4,6-bis(isopropylamino)-s-triazine, 2-chloro-4,6-bis(ethylamino)-s-triazine and 4-amino-6-tert.butyl-3-methylthio-1,2,4-triazin-5(4H)-one.

In general, antidotes are used in formulations containing the antidote and an inert carrier. The herbicides can be included in the same formulation if desired. Such formulations can take the form of dusts, wettable powders, granules, solutions of emulsifiable concentrates. Alternate methods of antidote application are well known, for example, the antidote can be incorporated into the soil before, after, or simultaneously with the herbicides. Solutions of antidote and herbicides can also be combined to form a tank mix which can be applied onto the surface of the soil or incorporated into the soil. In another method, the antidote can be directly applied into the seed furrow before or after crop seed placement, prior to covering the seeds with soil. This in-furrow method economically and effectively places the antidote immediately adjacent the crop seed to be protected from herbicidal injury. The in-furrow application can take place before or after the herbicides have been applied to the soil. It is also possible to treat the crop seeds with the antidote prior to planting.

As used in this specification, the term herbicide refers to a compound that selectively controls, prevents, or inhibits the growth of vegetation or plants. Herbicides are generally applied to the soil where control of undesired vegetation is sought. In agricultural use, the herbicide can be applied to the soil before, after or simultaneously with planting of the crop seeds. The amount of herbicide employed in a given situation will depend on the particular herbicide used, the crop to be grown in the field, the types of weeds to be controlled and the degree of control desired. Herbicides are usually employed at a rate of about 0.05 to about 50 pounds per acre with a rate of about 1.0 to about 20 pounds per acre being preferred.

In the herbicidal compositions of this invention the ratio of thiocarbamate to triazine will also vary depending on soil conditions, weeds to be controlled, etc. In general, a weight ratio of thiocarbamate to triazine of about 0.001–100:1, preferably about 0.01–50:1, will be used.

The term herbicide antidote refers to a compound which, when applied to the crop seed or the soil in which the crop seed is or will be planted, counteracts the growth controling injurious effect of the herbicide on the crop. The term antidotally effective amount refers to the amount of the antidote which when applied to the crop seed or soil achieves the desired protection of the crop. This amount will vary widely, depending on the particular herbicide used and the method of application of the antidote. One skilled in the art, with the teaching of this specification before him, will be able, without undue experimentation, to determine the antidotally effective amount of the N-benzenesulfonyl carbamate for a given application. The amount of antidote employed can range from about 0.05 to about 50 pounds per acre. A rate of application of about 1 to about 10 pounds per acre is preferred.

In general the amount of antidote compound used in proportion to the amount of herbicide used will be from about 0.001 to about 50, preferably about 0.01 to about 20, parts by weight of antidote per part herbicide.

What is claimed is:

1. A herbicidal composition comprising a herbicidally effective amount of a herbicidal mixture comprising a thiocarbamate and a triazine having a weight ratio of about 0.01–50:1, respectively, and an antidotally effective amount of a N-benzenesulfonyl carbamate of the formula

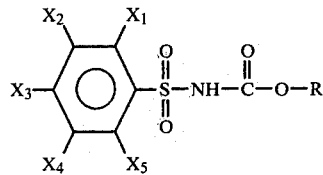

wherein each of $X_1$, $X_2$, $X_3$, $X_4$ and $X_5$ is independently selected from the group consisting of hydrogen, halogen and lower alkyl, with the proviso that when $X_3$ is lower alkyl, $X_1$ and $X_5$ are not both hydrogen; and R is selected from the group consisting of lower alkyl, alkenyl, alkynyl and alkyl and alkenyl radicals substituted with up to five halo atoms and wherein said N-benzenesulfonyl carbamate is present in proportion to the herbicide from about 0.01 to about 20 parts by weight, said N-benzenesulfonyl carbamates being antidotally active towards soybeans with said thiocarbamate and triazine herbicide mixture.

2. The composition of claim 1 wherein said thiocarbamate is S-n-propyl N,N-di-n-propyl thiocarbamate.

3. The composition of claim 1 wherein said triazine is 2-chloro-4-ethylamino-6-isopropyl-s-triazine.

4. The composition of claim 1 wherein said N-benzenesulfonyl carbamate is N-(p-chlorobenzenesulfonyl)propargyl carbamate.

5. The composition of claim 1 wherein said N-benzenesulfonyl carbamate is N-(p-chlorobenzenesulfonyl)-ethyl carbamate.

6. A method of protecting soybeans from herbicidal injury which comprises applying to the soil a herbicidally effective amount of a herbicidal mixture comprising a thiocarbamate and a triazine having a weight ratio of about 0.01–50:1, respectively, and an antidotally effective amount of an N-benzenesulfonyl carbamate of the formula

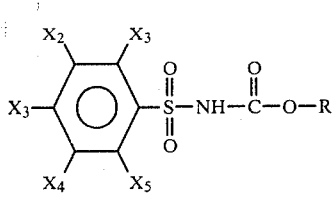

wherein each of $X_1$, $X_2$, $X_3$, $X_4$ and $X_5$ is independently selected from the group consisting of hydrogen, halogen, and lower alkyl, with the proviso that when $X_3$ is lower alkyl, $X_1$ and $X_5$ are not both hydrogen; and R is selected from the group consisting of lower alkyl, alkenyl, alkynyl and alkyl and alkenyl radicals substituted with up to five halo atoms and wherein said N-benzenesulfonyl carbamate is present in proportion to the herbicide from about 0.01 to about 20 parts by weight.

7. The method of claim 6 wherein said thiocarbamate is S-n-propyl N,N-di-n-propyl thiocarbamate.

8. The method of claim 6 wherein said triazine is 2-chloro-4-ethylamino-6-isopropylamino-s-triazine.

9. The method of claim 6 wherein said N-benzenesulfonyl carbamate is N-(p-chlorobenzenesulfonyl)propargyl carbamate.

10. The method of claim 6 wherein said N-benzenesulfonyl carbamate is N-(p-chlorobenzenesulfonyl)-ethyl carbamate.

* * * * *